(12) United States Patent
Zhang et al.

(10) Patent No.: US 11,890,465 B2
(45) Date of Patent: Feb. 6, 2024

(54) HYBRID SENSING AND STIMULATION UTILIZING PRE-PULSING OF WAVEFORMS

(71) Applicant: Boston Scientific Neuromodulation Corporation, Valencia, CA (US)

(72) Inventors: Tianhe Zhang, Studio City, CA (US); Rosana Esteller, Santa Clarita, CA (US); Natalie Brill, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 177 days.

(21) Appl. No.: 16/294,701

(22) Filed: Mar. 6, 2019

(65) Prior Publication Data

US 2019/0298992 A1 Oct. 3, 2019

Related U.S. Application Data

(60) Provisional application No. 62/648,475, filed on Mar. 27, 2018.

(51) Int. Cl.
*A61N 1/05* (2006.01)
*A61N 1/36* (2006.01)
(Continued)

(52) U.S. Cl.
CPC ....... *A61N 1/0553* (2013.01); *A61N 1/36062* (2017.08); *A61N 1/36125* (2013.01);
(Continued)

(58) Field of Classification Search
CPC ............ A61N 1/36062; A61N 1/37252; A61N 1/3787; A61N 1/36139; A61N 1/3758;
(Continued)

(56) References Cited

U.S. PATENT DOCUMENTS 6,516,227 B1   2/2003   Meadows et al.
6,560,490 B2   5/2003   Grill et al.
(Continued)

FOREIGN PATENT DOCUMENTS

WO   2012/155186 A1   11/2012
WO   2017/219096 A1   12/2017

OTHER PUBLICATIONS

International Search Report and Written Opinion regarding corresponding PCT Application No. PCT/US2019/021019, dated May 20, 2019.

(Continued)

*Primary Examiner* — Lynsey C Eiseman
*Assistant Examiner* — Amanda L Steinberg
(74) *Attorney, Agent, or Firm* — Lewis & Reese, PLLC

(57) ABSTRACT

Methods and systems for providing neuromodulation therapy are disclosed. The systems include an Implantable Pulse Generator (IPG) or External Trial Stimulator (ETS) that is capable of sensing an Evoked Compound Action Potential (ECAP), and (perhaps in conjunction with an external device) is capable of adjusting a stimulation program while based on the sensed ECAP. The stimulation program may include a pre-pulse component that may be adjusted based on the sensed ECAP. Moreover, stimulation may be applied to neural elements timed to coincide with the arrival of ECAPs at those neural elements. The stimulation may enhance or suppress activation of those neural elements.

18 Claims, 11 Drawing Sheets

(51) Int. Cl.
  *A61N 1/375* (2006.01)
  *A61N 1/378* (2006.01)
  *A61N 1/372* (2006.01)

(52) U.S. Cl.
  CPC ....... *A61N 1/36185* (2013.01); *A61N 1/3754* (2013.01); *A61N 1/3758* (2013.01); *A61N 1/36071* (2013.01); *A61N 1/36139* (2013.01); *A61N 1/3787* (2013.01); *A61N 1/37252* (2013.01)

(58) Field of Classification Search
  CPC . A61N 1/3754; A61N 1/36125; A61N 1/0553
  See application file for complete search history.

(56) References Cited

U.S. PATENT DOCUMENTS

| | | | |
|---|---|---|---|
| 7,024,247 | B2 | 4/2006 | Gliner et al. |
| 7,424,322 | B2 | 9/2008 | Lombardi et al. |
| 7,450,992 | B1 | 11/2008 | Cameron |
| 7,742,810 | B2 * | 6/2010 | Moffitt ............... A61N 1/36167 607/2 |
| 8,255,057 | B2 | 8/2012 | Fang et al. |
| 8,335,664 | B2 | 12/2012 | Eberle |
| 8,606,362 | B2 | 12/2013 | He et al. |
| 8,620,436 | B2 | 12/2013 | Parramon et al. |
| 8,768,453 | B2 | 7/2014 | Parramon et al. |
| 9,044,155 | B2 | 6/2015 | Strahl |
| 9,061,140 | B2 | 6/2015 | Shi et al. |
| 9,119,964 | B2 | 9/2015 | Marnfeldt |
| 9,248,274 | B2 | 2/2016 | Troosters et al. |
| 9,248,279 | B2 | 2/2016 | Chen et al. |
| 9,302,112 | B2 | 4/2016 | Bornzin et al. |
| 9,403,013 | B2 | 8/2016 | Walker et al. |
| 9,409,020 | B2 | 8/2016 | Parker |
| 9,526,897 | B2 | 12/2016 | Chen et al. |
| 9,731,116 | B2 | 8/2017 | Chen |
| 10,076,667 | B2 | 9/2018 | Kaula et al. |
| 2007/0142874 | A1 * | 6/2007 | John ...................... A61N 2/006 607/45 |
| 2010/0331916 | A1 | 12/2010 | Parramon et al. |
| 2012/0095529 | A1 | 4/2012 | Parramon et al. |
| 2014/0005752 | A1 * | 1/2014 | Hershey ............. A61N 1/36003 607/61 |
| 2014/0288551 | A1 * | 9/2014 | Bharmi .............. A61N 1/36121 606/41 |
| 2015/0328465 | A1 | 11/2015 | Tyler et al. |
| 2015/0360038 | A1 | 12/2015 | Zottola et al. |
| 2017/0056642 | A1 * | 3/2017 | Moffitt ................... G16H 50/20 |
| 2017/0259065 | A1 | 9/2017 | Baru et al. |
| 2018/0071513 | A1 | 3/2018 | Weiss et al. |
| 2018/0071520 | A1 | 3/2018 | Weerakoon et al. |

OTHER PUBLICATIONS

Grill, WM and Mortimer, JT. "Stimulus waveforms for selective neural stimulation" IEEE EMBS. vol. 14(4) 1995.

McIntyre CC, Grill WM., "Selective Microstimulation of Central Nervous System Neurons," Ann Biomed Eng., Mar. 2000, 28(3):219-33.

McIntyre CC, Grill WM., "Excitation of Central Nervous System Neurons by Nonuniform Electric Fields," Biophys Journal, vol. 76(2), Feb. 1999, pp. 878-888.

Merrill, Daniel R., et al., "Electrical Stimulation of Excitable Tissue: Design of Efficacious and Safe Protocols," Journal of Neuroscience Methods, 141, 2005, pp. 171-198.

Part No. MSP430 data sheet, manufactured by Texas Instruments, retrieved from <http://www.ti.com/lsds/ti/microcontroller/16-bit_msp430/overview.page?DCMP=MCU_other&HQS=msp430>.

Wolter, Tilman, "Spinal Cord Stimulation for Neuropathic Pain: Current Perspectives," Journal of Pain Research, Nov. 18, 2014, 7, pp. 651-663.

Extended European Search Report regarding corresponding European Patent Application No. 23165523.4, dated May 23, 2023.

* cited by examiner

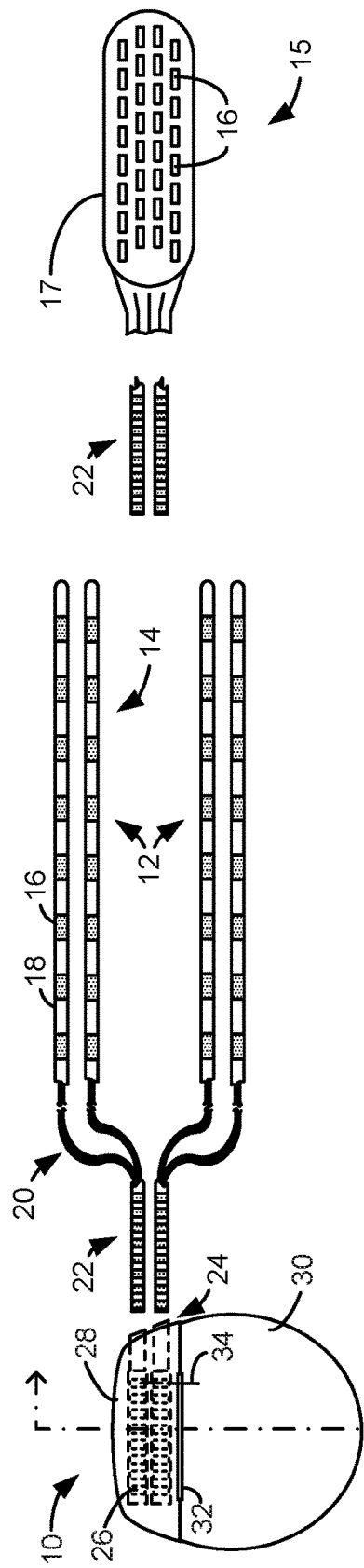
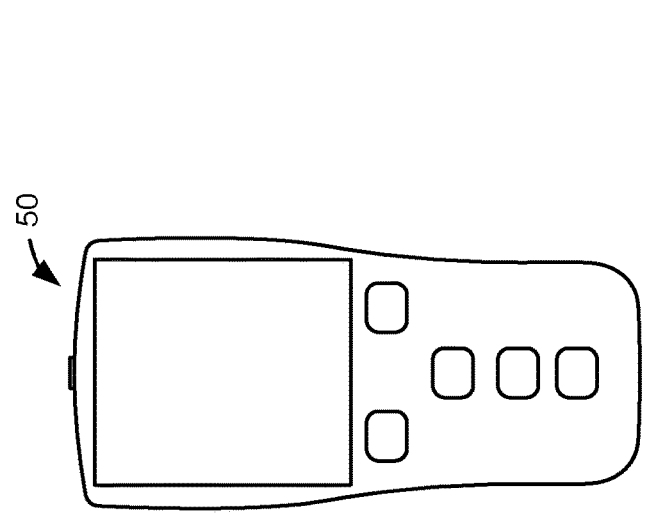
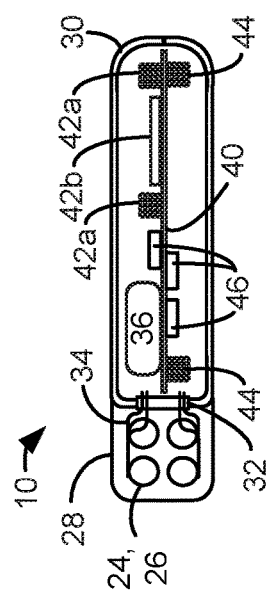
Figure 1A (prior art)
Figure 1B (prior art)
Figure 2 (prior art)

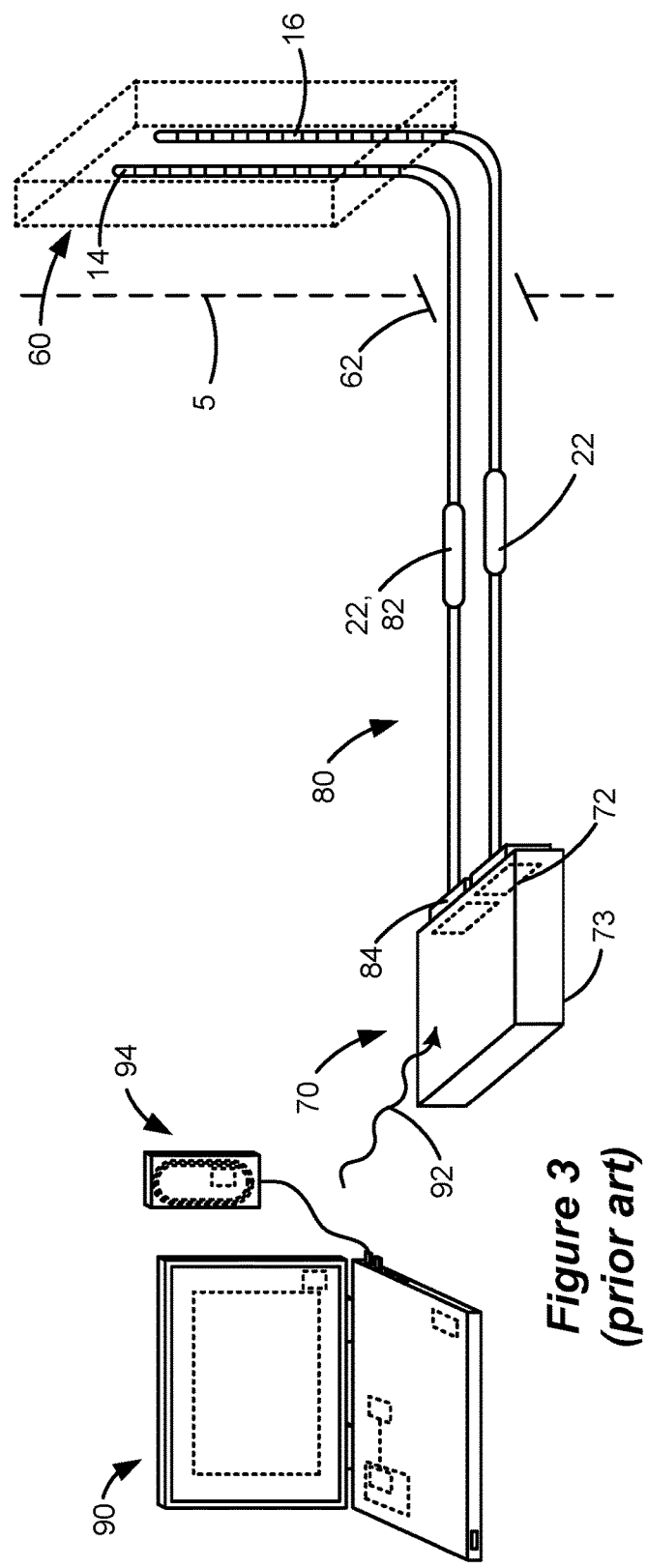
*Figure 3 (prior art)*
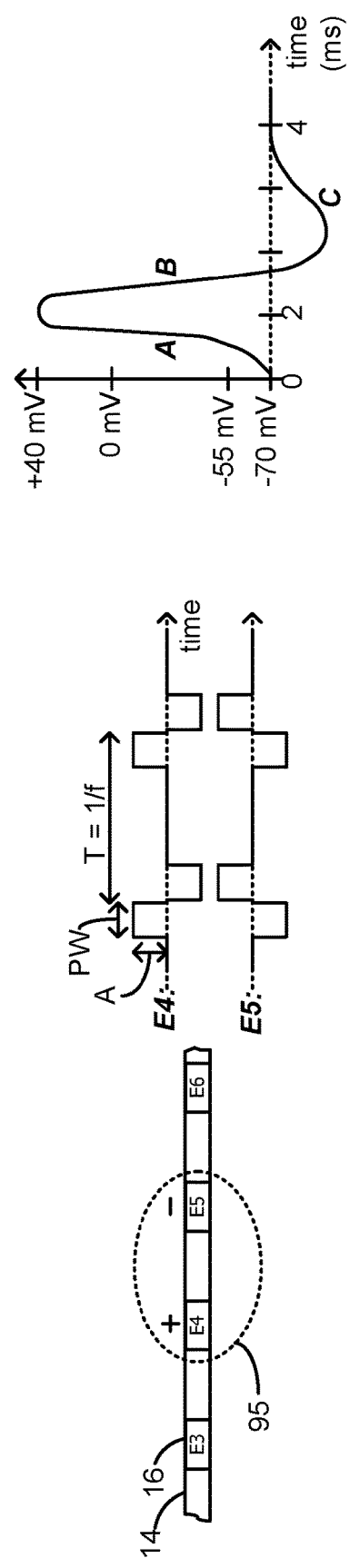
*Figure 5A*
*Figure 5B*
*Figure 6*

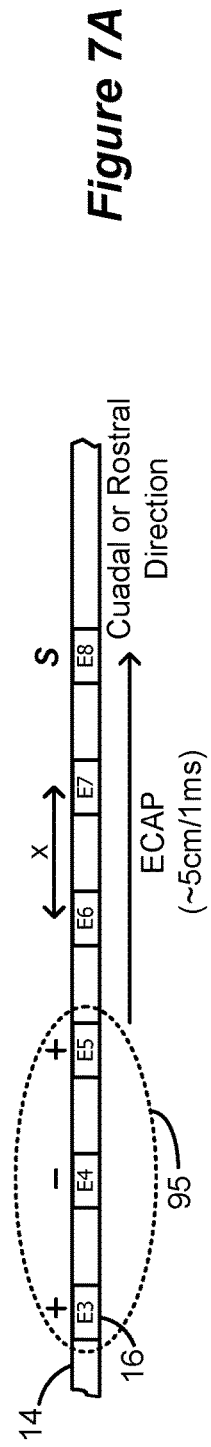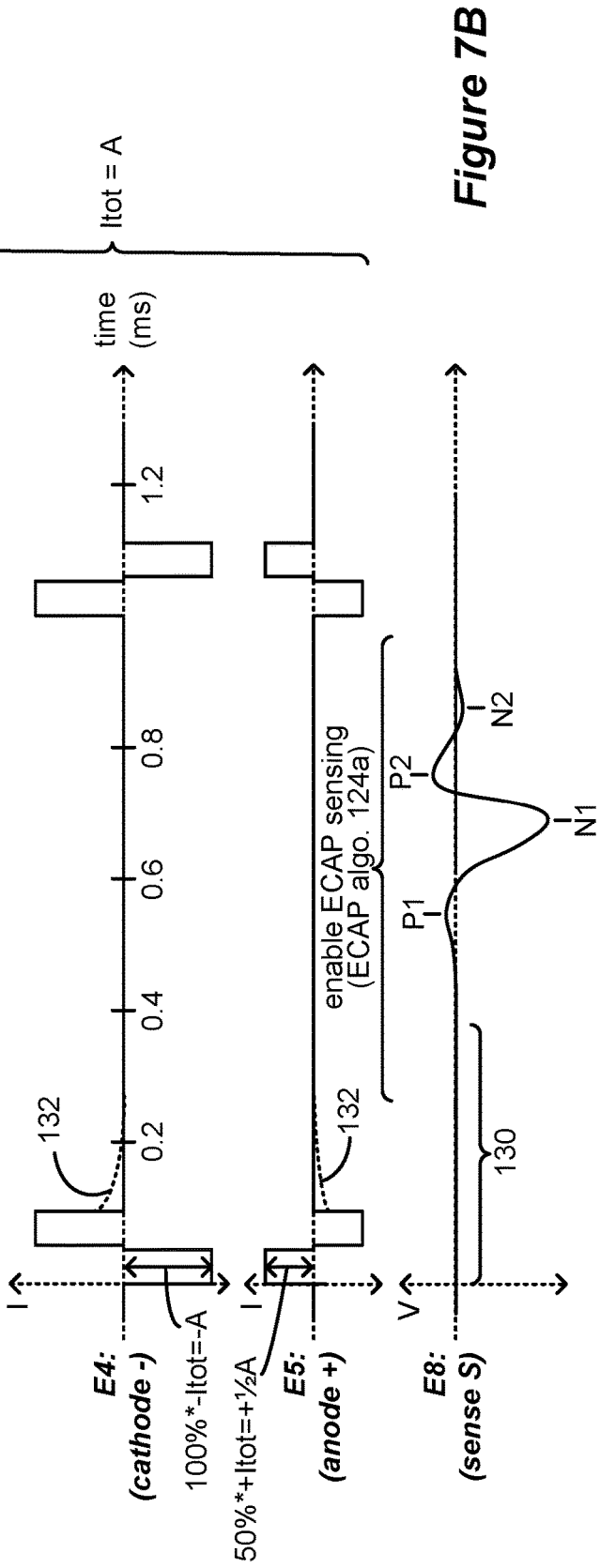

HYBRID SENSING AND STIMULATION UTILIZING PRE-PULSING OF WAVEFORMS

CROSS REFERENCE TO RELATED APPLICATIONS

This is a non-provisional of U.S. Provisional Patent Application Ser. No. 62/648,475, filed Mar. 27, 2018, to which priority is claimed, and which is incorporated herein by reference in its entirety.

FIELD OF THE INVENTION

The present invention relates generally to medical device systems, and more particularly to pulse generator systems operable to measure spinal cord potential (SCP) that can be used to adjust stimulation therapy.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and other neurological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which can be inserted into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14 (referred to as percutaneous leads), with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty-two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; a telemetry antenna—42a and/or 42b—for wirelessly communicating data with an external controller 50 (FIG. 2); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2), or a clinician programmer 90 (FIG. 3). Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS).

Implantation of IPG 10 in a patient is normally a multi-step process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

The stimulation program executed by the ETS 70 can be provided or adjusted via a wired or wireless link 92 (wireless shown) from a clinician programmer 90. As shown, the clinician programmer 90 comprises a computer-type device, and may communicate wirelessly with the ETS 70 via link 92, which link may comprise magnetic inductive or short-range RF telemetry schemes as already described. Should the clinician programmer 90 lack a communication antenna, a communication head or wand 94 may be wired to the computer which has a communication antenna. Thus, the ETS 70 and the clinician's programmer 90 and/or its communication head 94 may include antennas compliant with the telemetry scheme chosen. Clinician programmer 90 may be as described in U.S. Patent Application Publication 2015/0360038. External controller 50 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure.

By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined during the trial stimulation phase, it/they can then be programmed into the IPG 10, and thereafter modified wirelessly, using either the external programmer 50 or the clinician programmer 90.

SUMMARY

A neuromodulation system is disclosed herein. According to one embodiment, the neuromodulation system comprises: a first device comprising a non-transitory computer-readable medium comprising instructions configured to cause a microcontroller to: cause one or more primary stimulus electrodes implanted in a patient to issue first waveforms to the patient's neural tissue, receive signals from one or more sensing electrodes implanted in the patient, the signals indicative of a sensed neural response at the one or more sensing electrodes, determine a time interval between the issuing of the first waveforms and an arrival of the sensed neural response at the one or more sensing electrodes, and based on the determined time interval, trigger one or more secondary stimulus electrodes to issue second waveforms to the patient's neural tissue.

According to some embodiments, the one or more secondary stimulus electrodes do not include any of the one or more sensing electrodes. According to other embodiments, the one or more secondary stimulus electrodes includes at least one of the sensing electrodes.

According to some embodiments, the second waveforms comprise a pre-pulse component. According to some embodiments, the one or more secondary stimulus electrodes are sensing electrodes and the pre-pulse component is triggered before the neural response arrives at the one or more secondary stimulus electrodes. According to some embodiments, the pre-pulse component suppresses the neural response. According to some embodiments, the pre-pulse component enhances the neural response. According to some embodiments, the first device is an implantable pulse generator (IPG). According to some embodiments, the first device is an external programmer for an IPG. According to some embodiments, the one or more primary stimulus electrodes and the one or more sensing electrodes are comprised within percutaneous leads. According to some embodiments, the one or more primary stimulus electrodes and the one or more sensing electrodes are comprised within the same percutaneous lead. According to some embodiments, the one or more primary stimulus electrodes and the one or more sensing electrodes are comprised within different percutaneous leads. According to some embodiments, the one or more primary stimulus electrodes and the one or more sensing electrodes are comprised within paddle leads.

Also disclosed herein is a neuromodulation system comprising: a first device comprising a non-transitory computer-readable medium comprising instructions configured to cause a microcontroller to: cause one or more stimulation electrodes implanted in a patient to issue stimulation waveforms to the patient's neural tissue, wherein the stimulation waveforms comprise a pre-pulse component, receive signals from one or more sensing electrodes implanted in the patient, the signals indicative of a sensed neural response at the one or more sensing electrodes, determine a parameter of the sensed neural response, change the pre-pulse component of the stimulation waveform, and determine a correlation between changes in the pre-pulse component and changes in the parameter of the sensed neural response.

According to some embodiments, the parameter of the sensed neural response is a biomarker associated with one or more therapeutic effects or one or more neurological conditions. According to some embodiments, the non-transitory computer-readable medium further comprises instructions configured to cause the microcontroller to adjust the pre-pulse component so that the parameter of the sensed neural response is within a range.

Also disclosed herein is a non-transitory computer-readable medium comprising instructions configured to cause a microcontroller to: cause one or more primary stimulus electrodes implanted in a patient to issue first waveforms to the patient's neural tissue, receive signals from one or more sensing electrodes implanted in the patient, the signals indicative of a sensed neural response at the one or more sensing electrodes, determine a time interval between the issuing of the first waveform and an arrival of the sensed neural response at the one or more sensing electrodes, and based on the determined time interval, trigger one or more secondary stimulus electrodes to issue second waveforms to the patient's neural tissue.

According to some embodiments, the one or more secondary stimulus electrodes does not include any of the one or more sensing electrodes. According to some embodiments, the one or more secondary stimulus electrodes includes at least one of the sensing electrodes. According to some embodiments, the second waveforms comprise a pre-pulse component. According to some embodiments, the one or more secondary stimulus electrodes are sensing electrodes and wherein the pre-pulse component is triggered before the neural response arrives at the one or more secondary stimulus electrodes. According to some embodiments, the pre-pulse component suppresses the sensed neural response. According to some embodiments, the pre-pulse component enhances the sensed neural response.

BRIEF DESCRIPTION OF THE DRAWINGS

FIGS. 1A and 1B respectively show an Implantable Pulse Generator (IPG) in plan and cross-sectional views, in accordance with the prior art.

FIG. 2 shows a hand-held external controller for communicating with an IPG, in accordance with the prior art.

FIG. 3 shows a clinician programming system for communicating with an IPG or an External Trial Stimulator (ETS), in accordance with the prior art.

FIGS. 5A and 5B show a stimulation program.

FIG. 5 shows a graph of an action potential of a neuron.

FIG. 6 shows an electrical neural firing response produced in a patient's tissue from recruiting neurons.

FIGS. 7A and 7B show a stimulation waveform and an evoked compound action potential (ECAP).

DESCRIPTION

Figure 4A:
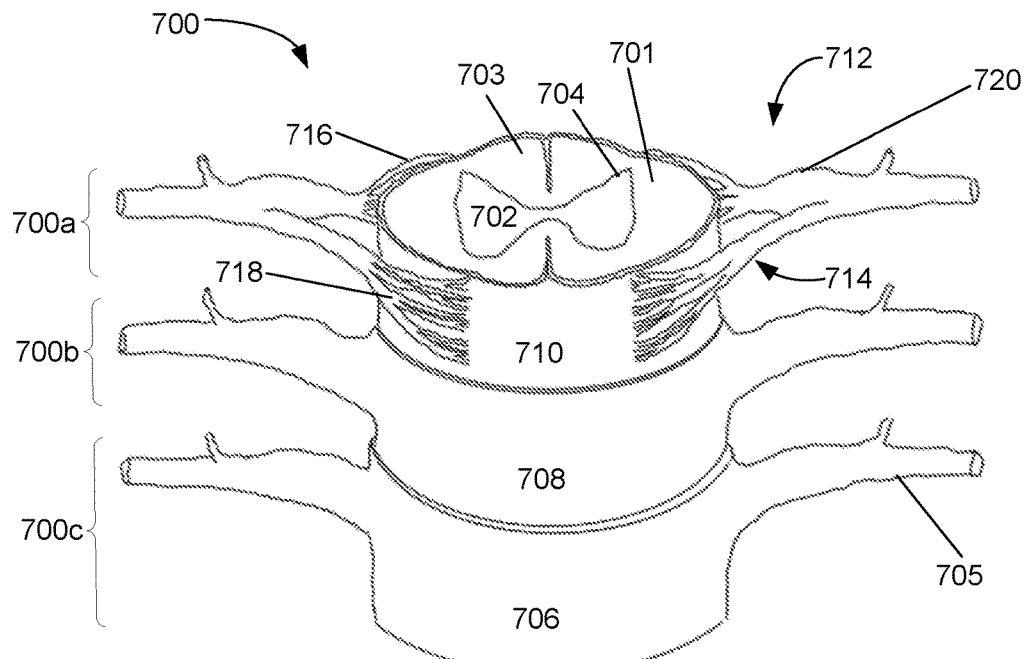
FIGS. 4A and 4B show aspects of the spinal cord and related neural anatomy
Figure 4B:
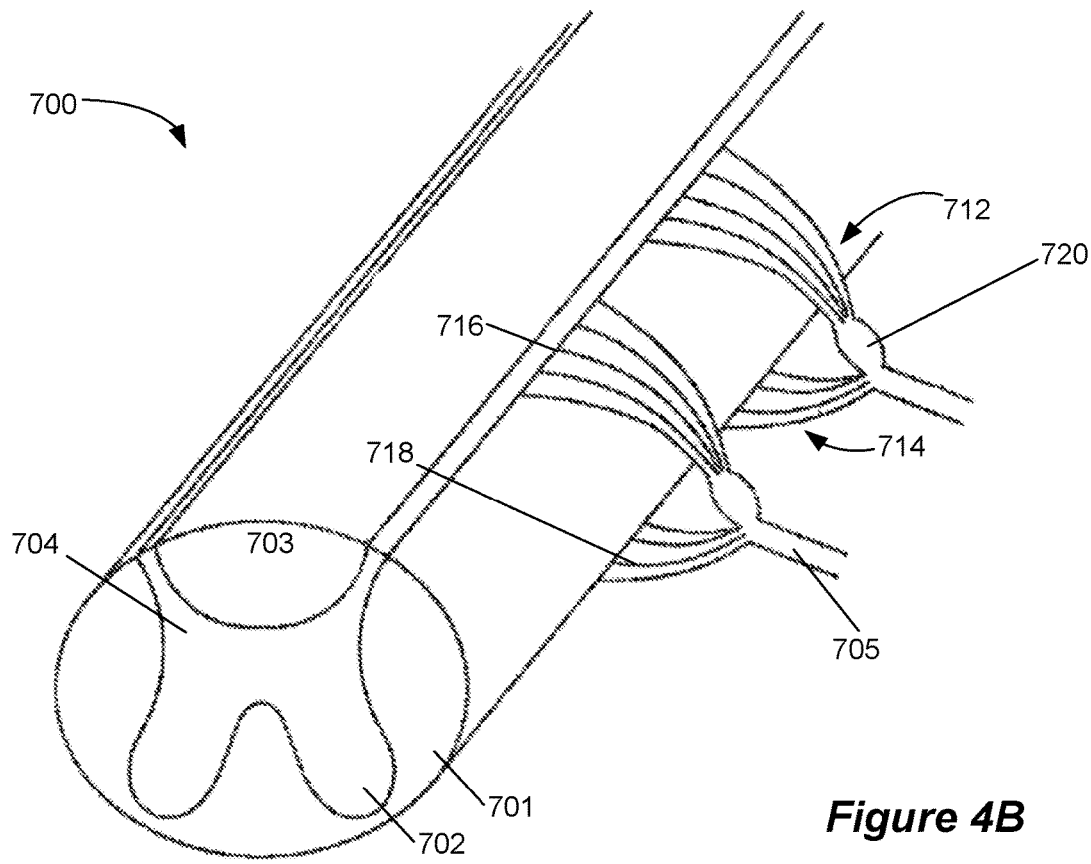

Various embodiments described herein involve spinal cord modulation, i.e., spinal cord stimulation (SCS) as well as stimulation and sensing of related neural anatomy. A brief description of the anatomy and physiology of the spinal cord is provided herein to assist the reader. FIGS. 4A and 4B illustrate, by way of example, a portion of a spinal cord 700 including white matter 701 and gray matter 702 of the spinal cord. A typical transverse section of the spinal cord includes a central "butterfly" shaped central area of gray matter 702 substantially surrounded by an ellipse-shaped outer area of white matter 701. The white matter of the dorsal column (DC) 703 includes mostly large myelinated axons that form afferent fibers that run in an axial direction. The dorsal portions of the "butterfly" shaped central area of gray matter are referred to as dorsal horns (DH) 704. In contrast to the DC fibers that run in an axial direction, DH fibers can be oriented in many directions, including laterally with respect to the longitudinal axis of the spinal cord. The gray matter 702 includes cell bodies, synapse, dendrites, and axon terminals.

Referring to FIG. 4A, the spinal cord is enclosed within three layers of tissue, collectively called the meninges. The outer layer of the meninges, called the dura mater 706, is shown in spinal cord segment 700c. The dura mater has been removed in spinal cord segment 700b to reveal the middle meninges, called the arachnoid 708. The innermost meninges, the pia mater 710, is shown in spinal cord segment 700a.

Examples of spinal nerves 705 are also illustrated. Upon removal of the meningeal layers, it is seen that each spinal nerve 705 splits into a dorsal root (DR) 712 and a ventral root 714, each of which comprise subdivisions referred to as rootlets. In FIG. 4A, the dorsal rootlets are labeled 716 and the ventral rootlets are labeled 718. The dorsal root also includes a structure called the dorsal root ganglion (DRG) 720, which comprises cell bodies of the afferent neurons. The dorsal root 712 contains afferent neurons, meaning that they carry sensory signals into the spinal cord, and the ventral root 714 functions as an efferent motor root. The dorsal and ventral roots join to form mixed spinal nerves 705.

An example of stimulation pulses as prescribed by an example stimulation program and as executable by the IPG or ETS 70 is illustrated in FIGS. 5A and 5B. As shown in FIG. 5A, electrode E4 is selected as the anode and electrode E5 is selected as the cathode. FIG. 5B illustrates the waveforms of the stimulation pulses delivered by E4 and E5. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses—having only a first pulse phase but not followed by an active-charge recovery second pulse phase—can also be used. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

When a neural fiber is recruited by electrical stimulation, it will issue an action potential—that is, the neural fiber will "fire." An action potential for a typical neural fiber is shown in FIG. 6. Should electrical recruitment from electrical stimulation cause the neural fiber's resting state (e.g., −70 mV as measured from inside the cell) to exceed a threshold (e.g., −55 mV), the neural fiber will depolarize ("A"), repolarize ("B"), and hyperpolarize ("C") before coming to rest again. If electrical stimulation continues, the neural fiber will fire again at some later time, though the neural fiber cannot fire again until after the membrane potential returns to the resting state after the hyperpolarization event. Note that the action potential does not change in magnitude for a given neural fiber. Instead, changing the strength of stimulation may affect the frequency at which action potentials are issued, and may also affect what types of neural fibers are recruited. Each neural fiber is unique in its shape and size, and thus can fire at its own inherent maximum frequency.

While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH 704 of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief.

Activation of large sensory DC nerve fibers in conventional SCS creates action potentials (i.e., nerve impulses) that propagate orthordromically (toward the brain) and antidromically (away from the brain) from the point of stimulation. The antidromic propagation of action potentials to fiber collaterals and terminals ending in the DH evokes pain control mechanisms within the DH, as described above. The orthodromic propagation of action potentials is responsible for the paresthesia sensation that often accompanies conventional SCS therapy.

The orthodromic and/or antidromic propagation of action potentials can be sensed at electrodes of the lead 14. Consider FIG. 7A, in which electrodes E3, E4 and E5 on lead 14 are used to produce pulses in a bipolar mode of stimulation, with E3 and E5 comprising an anode (+; or source of current) and E4 a cathode (−; or sink of current). Such stimulation produces an electromagnetic (EM) field in a volume 95 of the patient's tissue around the selected electrodes. Some of the neural fibers within the EM field volume 95 will be recruited and fire, particularly those proximate to the cathodic electrode E4. Hopefully the sum of the neural fibers firing within volume 95 will mask signals indicative of pain in an SCS application, thus providing the desired therapy.

The stimulation program is defined as before by various stimulation parameters to form stimulation pulses, such as which electrodes are active for stimulation, the polarity of those electrodes, the amplitude at selected electrodes, pulse width, pulse frequency, and stimulation waveform shape (square pulses in the example shown), although these parameters are not all labeled in FIG. 7B. In the example stimulation program shown, and considering only the first phase of the biphasic pulses, electrode E4 is selected to operate as a cathode (−), and electrodes E3 and E5 are selected to operate an anodes (+). Such stimulation is usually referred to as tripolar stimulation. Tripolar stimulation is one preferred mode of providing stimulation, particularly in an SCS application, because neural fibers in the dorsal column are activated proximate to the cathode. Tripolar stimulation generally allows effective stimulation to occur at lower current amplitudes.

In the example shown, the pulses are defined with respect to a total anodic and cathodic current (collectively, $I_{tot}$) that the electrodes will provide at any given time. This is desirable so that the patient's tissue will not receive a net amount of charge. The sole cathode electrode E4 provides all the total cathodic current ($-I_{tot}$), and so provides 100% ($-I_{tot}$), or −A. The two anode electrodes E3 and E5 must together issue the total anodic current ($+I_{tot}$), and in this example, each provides 50% ($+I_{tot}$), or +A/2. The anode electrodes can issue any anodic currents that together will equal $+I_{tot}$ (e.g., $70\%+I_{tot}$ and $30\%+I_{tot}$). It is assumed that this stimulation program has been chosen as one that generally provides good therapeutic results for a particular patient.

Neural fibers recruited and that fire within volume 95 create a cumulative response called an Evoked Compound Action Potential, or ECAP. Once stimulation begins (at time=0), an ECAP will be produced comprising the sum of the action potentials of neural fibers recruited and hence firing in volume 95. As shown in FIG. 7B, the ECAP will move through the patient's tissue via neural conduction with speeds of about 3.5-7.5 cm/ms in the typical case of Aβ fibers, or 0.3-3.5 cm/ms in the case of Aδ fibers. In the example shown, the ECAP moves to the right, which may be the orthodromic direction toward the brain (rostrally) or may be the antidromic direction toward the bottom of the spinal cord of the patient (caudally). Generally, the ECAP moves both rostrally and caudally from the point of stimulation. The amplitude of the ECAP will depends on how many neural fibers are firing. Generally speaking, a primary ECAP response, e.g., the height of peak P1, can vary, usually between tens of microVolts to tens of milliVolts.

It should be noted here that compound action potentials may be evoked in various neural elements, including the neural fibers of the dorsal column, the dorsal root fibers, the dorsal root ganglia, etc. As used herein, the ECAP refers to action potentials evoked in any of the neural elements. As explained further below, an ECAP is a neural response that can be sensed at an electrode.

Referring again to FIGS. 7A and 7B, a single sense electrode (S) has been chosen to sense the ECAP as it moves past, which in this example is electrode E8. Selection of an appropriate sense electrode can be determined by an ECAP algorithm operable in the control circuitry of the IPG based on a number of factors. For example, it is preferable that a sense electrode S be sensibly chosen with respect to the active electrodes, such that the EM field produced around the active electrodes will dissipate (or more preferably, cease) at the sense electrode by the time the ECAP arrives. This simplifies ECAP detection at the sense electrode, because voltages present in the EM field will not interfere with and potentially mask the ECAP at the sense electrode. (Note that the stimulation artifact resulting from the EM field is not shown at the sense electrode E8 for simplicity). To choose a sense electrode, the ECAP the algorithm (described below) preferably knows the pulse width of the pulses being issued, the extent of the size of the EM field (which can be estimated), the speed at which the ECAP is expected to travel, and the distance (x) between electrodes 16 in the electrode array 12, e.g., along a particular straight lead 14 or a paddle lead 15 (FIG. 1A).

In FIGS. 7A and 7B, for example, assume that the pulse width (of both phases of the biphasic pulses) is 0.1 ms as shown, and that sense electrode E8 is generally 2.0 cm away from the active electrodes (and hence their EM field). When the ECAP starts to form at time=0, it will arrive at electrode E8 after some delay 130 in accordance with the speed at which the ECAP moves (e.g., 5 cm/1 ms). In this example, the ECAP will start to pass sense electrode E8 at 0.4 ms. Thus, the ECAP algorithm can thus enable sensing of the ECAP starting at or before time=0.4 ms after the start of the stimulation pulse. Sensing can last for as long as necessary to detect at least some aspects of the shape and size of the resulting ECAP. For example, sensing can last for a long enough time to allow the polarization and refraction peaks in the ECAP to be detected, which may comprise up to 3 ms for example. If the total duration of the ECAP is longer than the quiet period between two subsequent pulses, e.g., between pulses 133a and 133b, subsequent pulses 133b may not be enabled until the ECAP measurement has finished.

Figure 8:
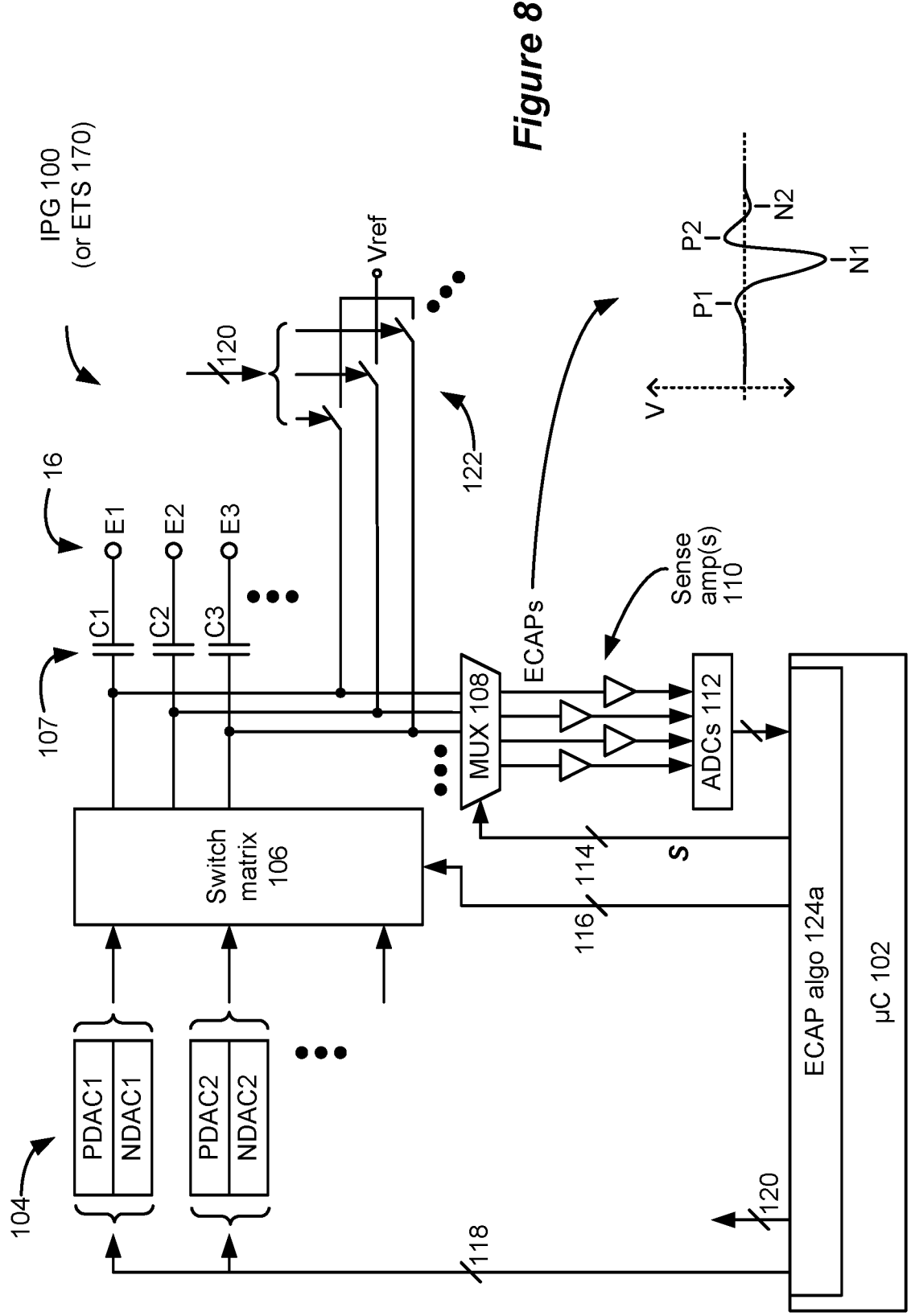
FIG. 8 shows aspects of circuitry for sensing ECAPs and modifying stimulation based on an algorithm using ECAP parameters.

FIG. 8 shows circuitry for an improved IPG 100 operable with the disclosed technique for sensing ECAP and using the sensed ECAP as a biomarker for directing therapy, as described further below. Although described in the context of an IPG 100, it should be realized that the disclosed technique could also be operable in an improved external stimulator, such as an External Trial Stimulation 170 that generally mimics the operation of an IPG as explained earlier.

The IPG 100 (or ETS 170) includes control circuitry 102 into which an ECAP algorithm 124a can be programmed. Control circuitry 102 may comprise a microcontroller for example such as Part Number MSP430, manufactured by Texas Instruments, which is described in data sheets at www.ti.com, which is incorporated herein by reference. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and USPs 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The illustrated circuitry for producing stimulation pulses and delivering them to the electrodes is merely one example. Other approaches may be found for example in U.S. Pat. Nos. 8,606,362 and 8,620,436, and U.S. Provisional Patent Application Ser. No. 62/393,003, filed Sep. 10, 2016. Note that a switch matrix 106 isn't required, and instead a PDAC and NDAC can be dedicated to (e.g., wired to) each electrode.

Notice that the current paths to the electrodes 16 include the DC-blocking capacitors 107 alluded to earlier, which as known, provide additional safety by preventing the inadvertent supply of DC current to an electrode and to a patient's tissue. As discussed earlier, capacitances such as these can become charged as stimulation currents are provided, providing an impetus for the use of biphasic pulses.

One or more of the electrodes 16 can be used to sense the ECAP described earlier, and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP, described further below, is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs.

Notice that connection of the electrodes 16 to the sense amp(s) 110 preferably occurs through the DC-blocking capacitors 107, such that capacitors are between the electrodes and the sense amp(s) 110. This is preferred so as to not undermine the safety provided by the DC-blocking capacitors 107.

Figure 11:
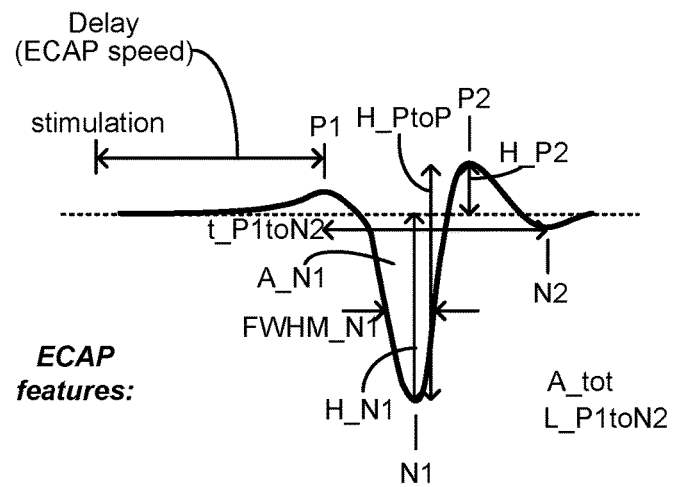
FIG. 11 shows various ECAP parameters.

Once the digitized ECAP is received at the control circuitry 102, it is processed by the ECAP algorithm 124a to determine one or more ECAP features that describe the basic shape and size of the ECAP(s), as explained further below with reference to FIG. 11. The response to stimulation can include potentials observed at different delays corresponding to different type of neural elements recruited. The delay from the stimulus can depend on the distance between the sensed electrode and the activation region where the electrical stimulus recruited most neural elements. Neural elements include axon fibers, neuron cell bodies, neuron dendrites, axon terminals, locations where fiber collaterals branch, interneurons, glial cells, or any nervous system functional part. In the specific case of the spinal cord, the sense electrodes can be placed over the dorsal column, more laterally in the epidural space towards and over the edge of dorsal horn and/or Lissauer's tract, over the dorsal root entry zone (DREZ), the rootlets, the dorsal root ganglia (DRG), the cauda equina region, the spinal nerves close to the spinal cord, the Spino-thalamic tract, and any other of the tracts surrounding the gray matter of the spinal cord. An ECAP can contain a number of peaks or waves indicative of the different phases of the averaged or compound action potential sensed and depending on the delay with respect to the stimulus, the peak potentials can be indicative of different type of fibers activated. Axon fibers with different functions (C fibers, Aβ fibers, Aδ fibers, and others) have different diameters that correlate with different propagation velocities for the compound potentials. Conduction velocities for different axonal fiber types are known, and the conduction velocities of the ECAPs sensed in the spinal cord can be calculated to determine the originating fiber. As shown, peaks in the ECAP are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG.

8 (and FIG. 11), because an ECAP's shape is a function of the number and types of neural fibers that are recruited in a given volume 95.

Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is within a range that the control circuitry 102 in the IPG 100 can handle, such as between 3 Volts and ground.

The inventors have discovered that sensed ECAPs can be used to direct the timing, location, and shape at which stimulation is applied to a patient's neural anatomy to maximize therapeutic response and/or minimize side effects of stimulation. In particular, the inventors have discovered that sensed ECAPs can be used as a biomarker for directing pre-pulsing of neural stimulation.

Figure 9:
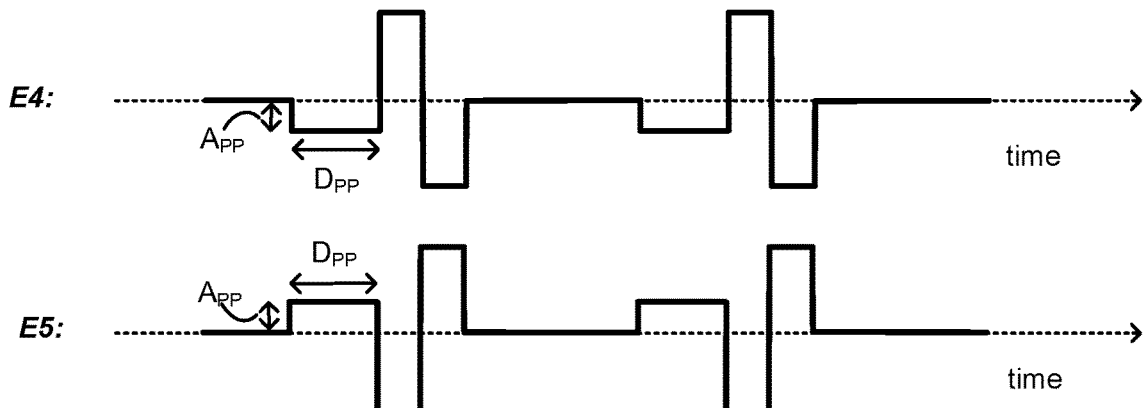
FIG. 9 shows stimulation waveforms with pre-pulsing components.

The term "pre-pulse," as used herein, refers to a relatively low-amplitude portion of a waveform that is provided at an electrode prior to providing a stimulation pulse. Pre-pulsing is illustrated in FIG. 9. FIG. 9 shows waveforms like those shown in FIG. 5B, except that the anodic pulse delivered at the electrode E4 is preceded by a cathodic pre-pulse having an amplitude $A_{PP}$ and a duration $D_{PP}$. Likewise, the cathodic pulse delivered at the electrode E5 is preceded by an anodic pre-pulse having an amplitude $A_{PP}$ and a duration $D_{PP}$. Pre-pulsing may be used to increase excitation of target fibers or to suppress or inhibit particular fibers. Whether excitatory or inhibitory 'priming' occurs depends on the polarity of the pre-pulse, and this polarity can be set according to the geometry and orientation of the target neural element(s).

Figure 10:
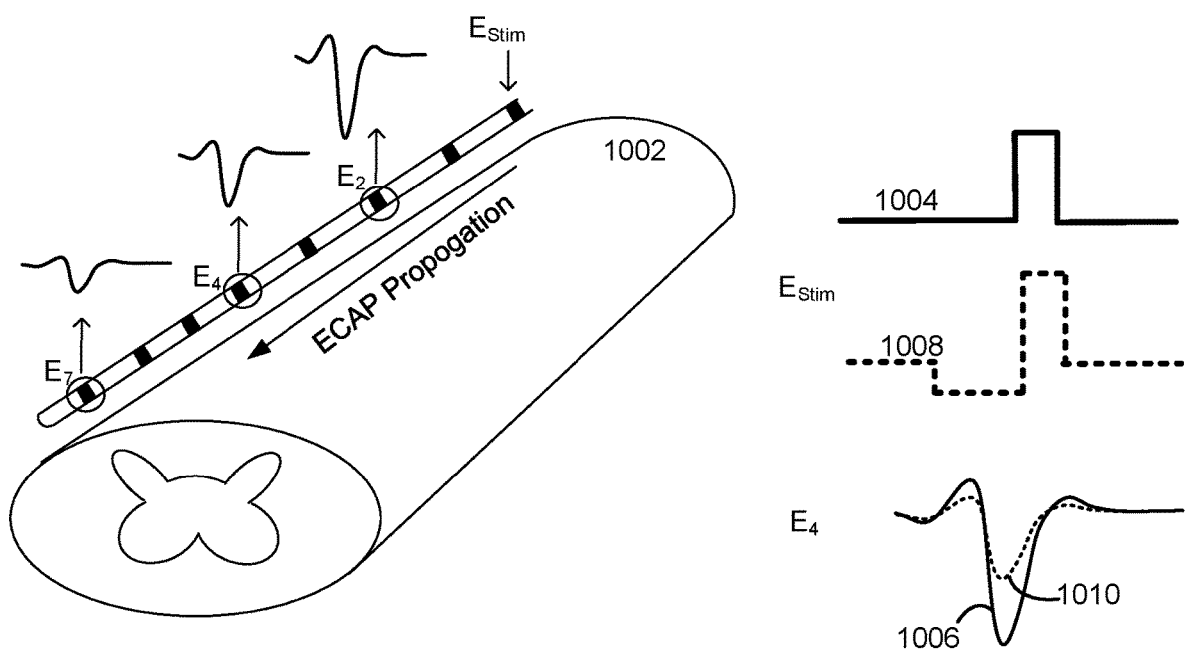
FIG. 10 shows ECAP propagation and the influence of pre-pulsing on sensed ECAPs.

FIG. 10 illustrates how pre-pulsing can influence sensed ECAPs. Assume that a monopolar monophasic stimulation pulse 1004 is applied at an electrode $E_{Stim}$. An ECAP may propagate through neural elements of the spinal cord 1002 and may be sensed at electrodes E2, E4, and/or E7, for example, as described above. For example, an ECAP sensed at the electrode E4 may have a shape 1006 in response to the pulse 1004. Now assume that a different stimulation pulse 1008, which includes a cathodic pre-pulse is applied at $E_{Stim}$. The resulting ECAP measured at the electrode E4 may have a different shape 1010 due to differences in neural recruitment caused by the pre-pulse. Thus, sensed ECAP provides a biomarker for neural recruitment differences arising because of differences in stimulation pre-pulsing (or differences in the stimulation waveform, in general).

According to certain embodiments described herein, one or more metrics are derived or calculated from sensed ECAPs. The metrics generally relate to features of the shapes of the sensed ECAPs. Once derived or calculated the metric(s) can be correlated to the therapeutic effectiveness of various stimulation waveforms, and in particular, waveforms having various pre-pulsing components. Features of an ECAP that can generate such metrics are shown in FIG. 11. These include (but are not limited to):

- a height of any peak (e.g., H_N1) present in the ECAP;
- a peak-to-peak height between any two peaks (such as H_PtoP from N1 to P2);
- a ratio of peak heights (e.g., H_N1/H_P2);
- a peak width of any peak (e.g., the full width half maximum of a N1, FWHM_N1);
- an area under any peak (e.g., A_N1);
- a total area (A_tot) comprising the area under positive peaks with the area under negative peaks subtracted or added;
- a length of any portion of the curve of the ECAP (e.g., the length of the curve from P1 to N2, L_P1toN2)
- any time defining the duration of at least a portion of the ECAP (e.g., the time from P1 to N2, t_P1toN2);
- a time delay from stimulation to issuance of the ECAP, which is indicative of the neural conduction speed of the ECAP, and which can be useful in discerning the types of neural fibers recruited;
- any mathematical combination or function of these variables (e.g., H_N1/FWHM_N1 would generally specify a quality factor of peak N1);
- metrics derived using mathematical/signal processing analysis of ECAP waveforms, such as short time Fourier or wavelet transforms, principal component analysis and/or eigenvalues from principal component analysis used as coefficients for k-means clustering, etc.

Figure 12:
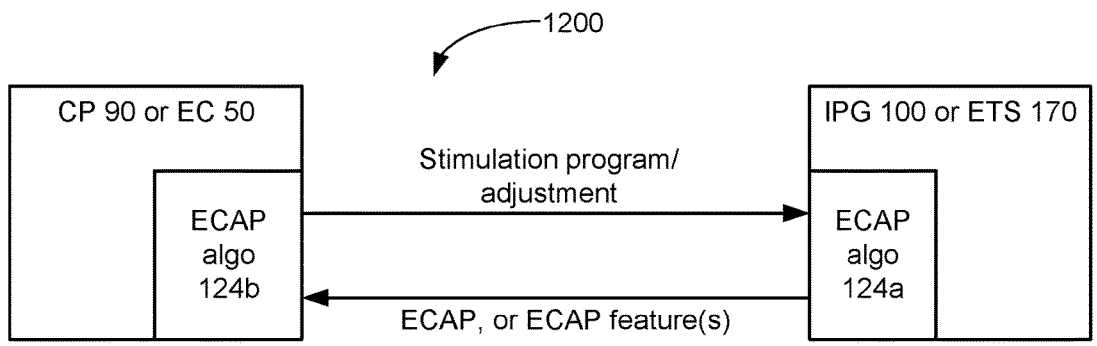
FIG. 12 shows a system using sensed ECAP parameters to control aspects of stimulation.

FIG. 12 illustrates aspects of a system 1200 for sensing ECAPs and using metrics derived from the sensed ECAPs to as a biomarker to determine the shape and timing of priming pulses (i.e., pre-pulses) to alter end-effector function. One aspect of the system 1200 is an improved IPG 100 (or ETS 170), as described above, with reference to FIG. 8. As mentioned above, the IPG 100 (or ETS 170) includes control circuitry 102 into which an ECAP algorithm 124a can be programmed. As also noted above, the ECAP algorithm can alternatively operate with the assistance of external devices, as shown in FIG. 3, which shows an external programming device (such as the clinician programmer 90 or external controller 50) in wireless communication with the IPG 100 (or ETS 170). Thus, another aspect of the system 1200 may be an external device, such as a CP 90 (or EC 50). An ECAP algorithm 124b is included in the external device, which can receive information from the IPG 100 (or ETS 170) regarding the ECAPs it measures, process the ECAP, and send a stimulation program (or adjustment) to the IPG. ECAP algorithm 124a again operates in the IPG 100 (or ETS 170), but in this example off-loads ECAP analysis and stimulation program adjustment to ECAP algorithm 124b in the external device. A system 1200 as shown in FIG. 12 is particularly useful when fitting the implant patient, i.e., when determining a stimulation program that would be useful in treating the patient's symptoms. One skilled in the art will understand that the ECAP algorithm 124a and 124b and/or any supporting user interface program will comprise instructions that can be stored on non-transitory machine-readable media (i.e., computer-readable medium), such as magnetic, optical, or solid-state memories. Such memories may be within the IPG or ETS itself (i.e., stored in association with control circuitry 102), within the external system, or readable by the external system (e.g., memory sticks or disks). Such memories may also include those within Internet or other network servers, such as an implantable medical device manufacturer's server or an app store server, which may be downloaded to the external system.

Figure 13:
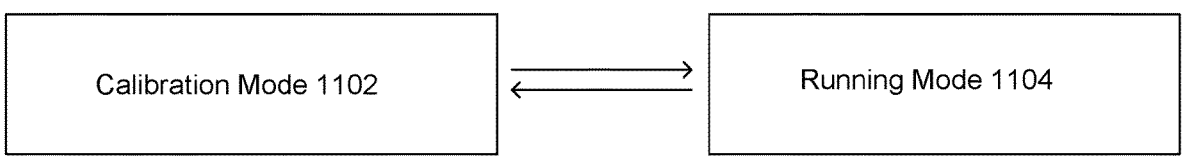
FIG. 13 shows sensing operation modes of an ECAP algorithm.

Referring to FIG. 13, embodiments of the neuromodulation system and algorithm may comprise two sensing operating modes (SOMs) 1100—a calibration mode 1102 and a running mode 1104. The calibration mode 1102 will typically be executed during the fitting process with the aid of the clinician programmer (CP) 90, though aspects of the calibration mode may be executed using the external controller (EC) 50. During the calibration mode 1102, the user, typically a clinician, is presented with a user interface, such as a graphical user interface (GUI). The interface is configured to present the user with a representation of the electrical signals provided to and sensed at the various available implanted electrodes (channels). The interface also allows user to modify the stimulation parameters of the IPG 100 and to visualize how changing the stimulation parameters affects the sensed ECAPs. An example of a system for interacting with the IPG 100 is described in "Precision Spectra™ System Programming Manual," Boston Scientific Corp., 90834018-18 Rev A (2016). The running mode 1104 is generally executed by programmed circuitry within the IPG 100 (or ETS 170), as described with reference to FIG. 8.

Figure 14A:
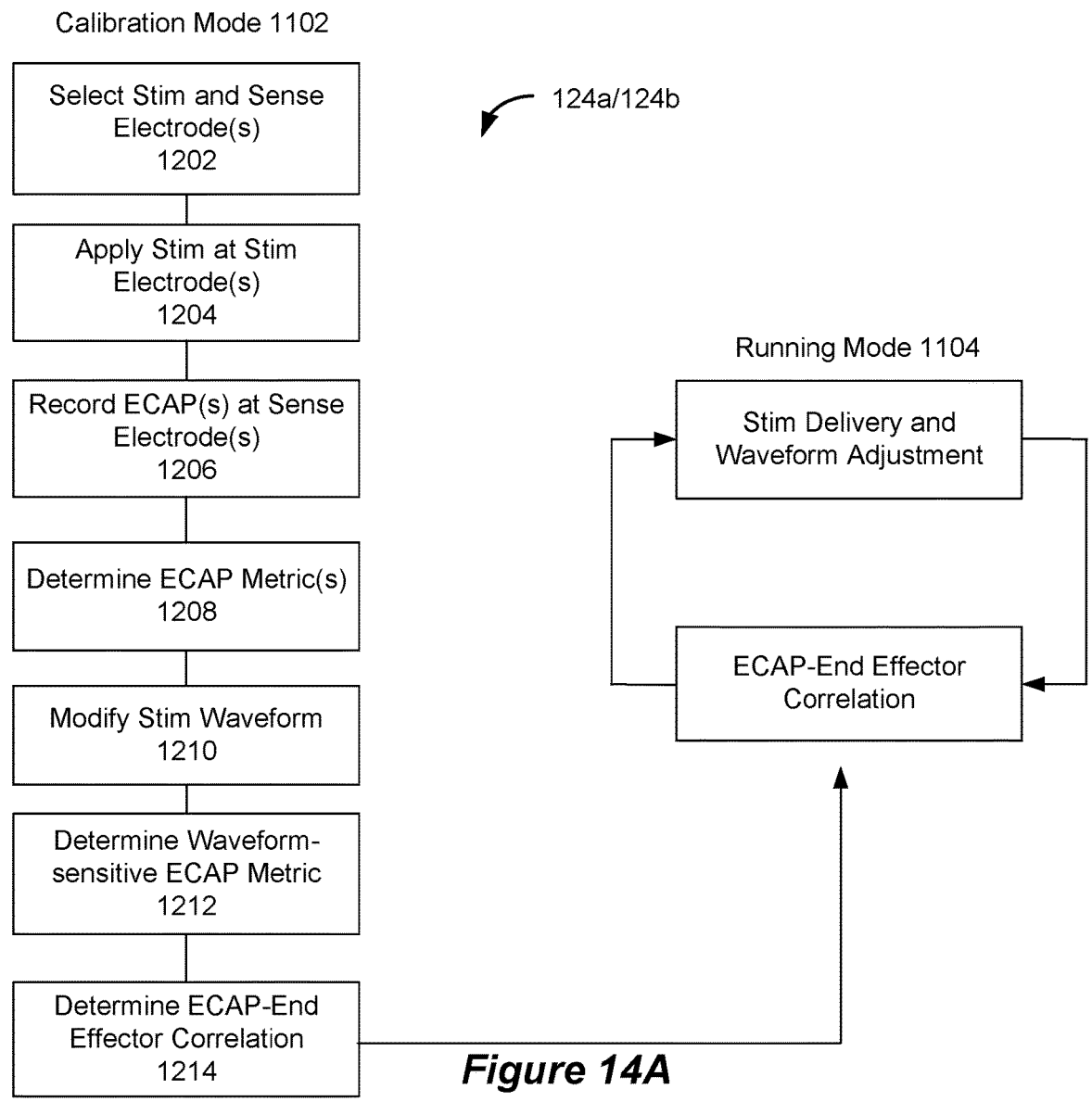
FIGS. 14A and 14B show aspects of an ECAP algorithm.
Figure 14B:
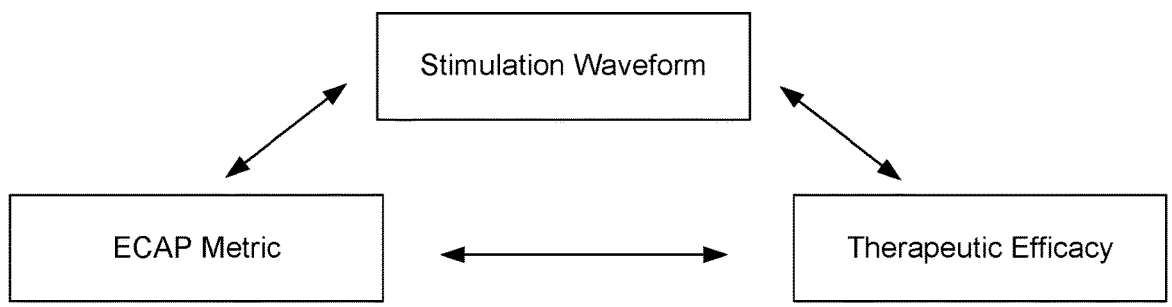

FIGS. 14A and 14B show an example of an algorithm 124a/124b for using sensed ECAPs to calibrate the shape and timing of priming pulses (i.e., pre-pulses) to alter end-effector function and to use the calibrated waveform-ECAP relationship to monitor and direct stimulation in a closed loop manner during a running mode. The algorithm 124a/124b allows a user, typically a clinician, to select stimulation electrode(s) and electrode(s) to use as sense electrodes for sensing ECAPs 1202. As explained above, the user will generally interact with a user interface on a programming device such as the clinician's programmer 90 to make those selections. Once stimulation and sense electrodes are selected, the user can apply a baseline stimulation waveform at the stimulation electrode(s) 1204. The baseline stimulation waveform may have an amplitude, frequency, pulse width, and waveform shape predicted to elicit a desired neurological response. ECAPs evoked in response to the stimulation electrode(s) are sensed and recorded at the sense electrode(s) 1206. The algorithm determines one or more metrics based on the recorded ECAPs 1208, as described above with relation to FIG. 11. The algorithm then modifies one or more features of the baseline stimulation waveform 1210. For example, the algorithm may modify an aspect of the pre-pulsing phase of the waveform. The algorithm then determines a correlation between the waveform modification and one or more of the ECAP metrics determined in step 1208. In other words, the algorithm determines how the ECAP metrics change in response to changes to the stimulation waveform to identify one or more waveform-dependent ECAP metrics 1212. According to some embodiments, it is useful to identify one or more particular ECAP metrics (e.g., H_N1, H_N1/H_P2, etc.) that are particularly sensitive to changes in the stimulation waveform. The algorithm develops a correlation describing how altering the waveform shape (e.g., pre-pulse polarity, duration, etc.) affects the recorded ECAP signal properties. Such correlations may be encoded into a look-up table, internal decision tree, or other storage medium. Having identified one or more waveform-sensitive ECAP metric(s) and having identified how altering the waveform shape affects the metric(s), the algorithm attempts to further adjust and optimize the stimulation waveform to arrive at the best therapeutic benefit. For example, the stimulation waveform can be adjusted based on patient feedback, 2-point discrimination tests, bio-signals such as heart rate, blood pressure, movement, temperature, and the like. An ECAP-end effector correlation is developed 1214 by monitoring the determined waveform-sensitive ECAP metric(s) during the optimization. Thus, the calibration mode determines an interrelationship between (1) stimulation waveform parameters, (2) ECAP metric parameters, and (3) therapeutic efficacy, as shown in FIG. 14B. The correlation can then be used to adjust the stimulation waveform delivery during the running mode of the algorithm 1104. For example, the stimulation parameters may be monitored and adjusted to maintain the selected waveform-sensitive metric within a predetermined range with respect to the metric value corresponding to the optimum therapy.

Figure 15:
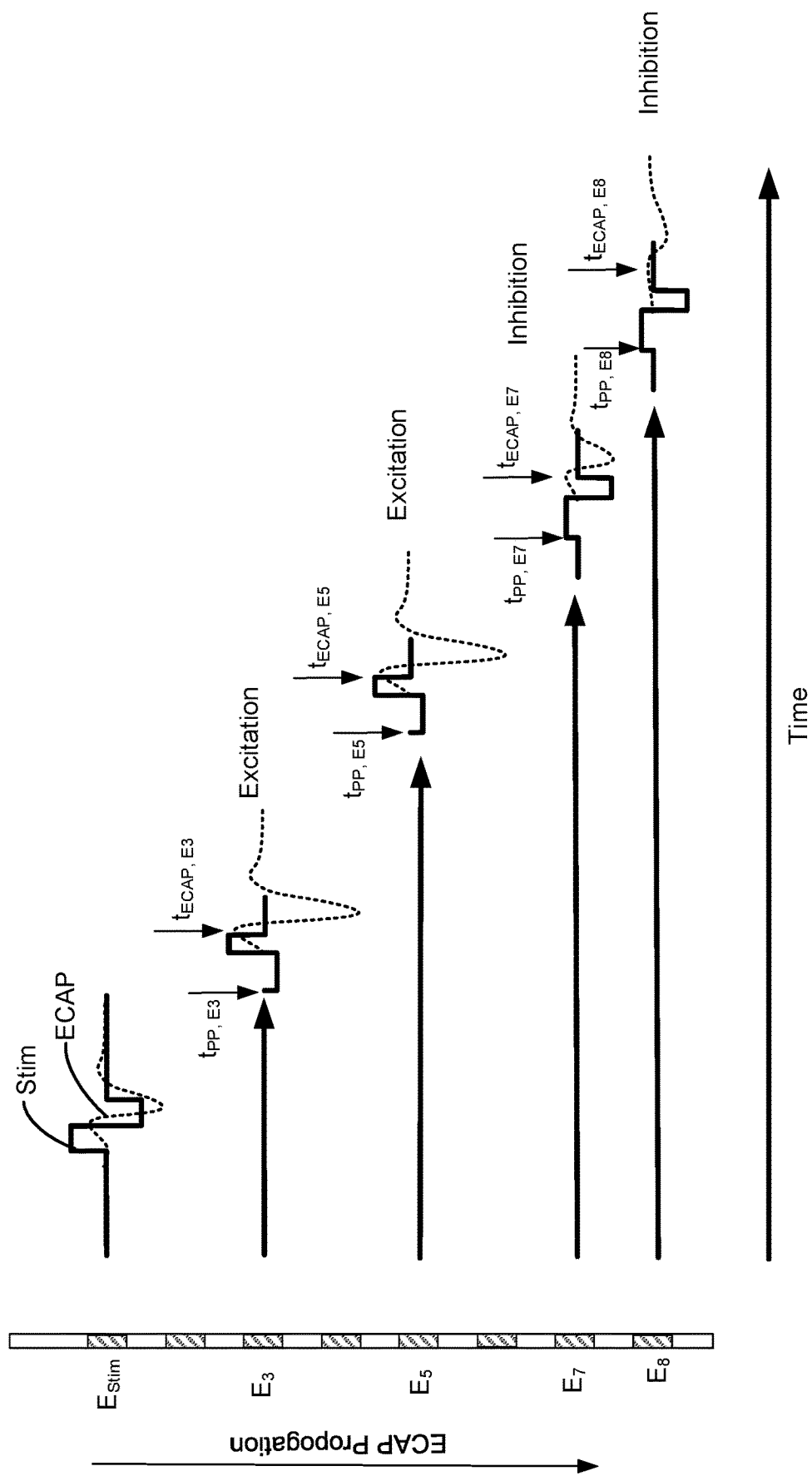
FIG. 15 shows aspects of an ECAP algorithm.

FIG. 15 illustrates examples of methods for using sensed ECAPs to tune shape and pulse sequence elements of waveforms delivered through multiple channels (i.e., at multiple electrodes) to either excite or inhibit neurological responses. In the multi-channel embodiments described herein, stimulus waveforms are issued at one or more electrodes, referred to herein as primary stimulus electrodes. The embodiment illustrated in FIG. 15 shows a single primary stimulus electrode $E_{Stim}$. However, more than one primary stimulus electrode may be used, for example, to apply bipolar or tripolar pulses. ECAPs are sensed at one or more sensing electrodes. Based on the sensing, additional stimulus waveforms are issued at electrodes, referred to herein as secondary stimulus electrodes. The secondary stimulus electrodes may be the same or different electrodes used as the sensing electrodes. In the embodiment illustrated in FIG. 15, the same electrodes (E3, E5, E7, and E8) are used both as sensing electrodes and as secondary stimulus electrodes. In the embodiment illustrated in FIG. 16B, different electrodes are used as sensing electrodes and as secondary stimulus electrodes. Namely, electrode E3 is used as a sensing electrode and electrodes E7 and E8 are used as secondary stimulation electrodes.

Referring to FIG. 15, assume that a biphasic stimulation waveform Stim applied at the electrode labeled $E_{Stim}$ evokes an ECAP. The ECAP propagates along the neural tissue and may be sensed at the electrode E3 at a time $t_{ECAP, E3}$, at the electrode E5 at a time $t_{ECAP, E5}$, at the electrode E7 at a time $t_{ECAP, E7}$, and at the electrode E8 at a time $t_{ECAP, E8}$. The times $t_{ECAP, E3}$, $t_{ECAP, E5}$, $t_{ECAP, E7}$, and $t_{ECAP, E8}$ can be determined in a calibration mode whereby the stimulation electrode $E_{Stim}$ applies a stimulation pulse and the time it takes the ECAPs to be sensed at the sense electrodes E3, E5, E7, and E8 is recorded and stored. The stored propagation times can then be used to trigger either excitation or inhibition pulses delivered at those electrodes to correspond with the arrival of the ECAP. According to some embodiments, the excitation or inhibiting waveforms may include a priming or pre-pulsing component that is triggered before the arrival of the ECAP. For example, assume that an excitation pulse is to be applied at E3 at a time $t_{ECAP, E3}$ corresponding to the arrival of the ECAP at E3. The ECAP arrival time $t_{ECAP, E3}$ is known from the calibration. A pre-pulse may be applied at E3 at time $t_{pp}$, E3 preceding the arrival of the ECAP. It should be noted that in the waveform shown at E3 in FIG. 15, the charge passed in the pre-pulse phase of the waveform equals the charge passed during the "active" phase of the waveform. Thus, the charges are balanced. However, according to some embodiments, the charges may be unbalanced and passive recovery may be used to recover the charge of the pre-pulse or of the active phase.

In the embodiment illustrated in FIG. 15, electrodes E3 and E5 are configured to provide excitation waveforms and electrodes E7 and E8 are configured to provide inhibition waveforms. The waveforms provided at E3, E5, E7, and E8 are each triggered to correspond to the arrival of the ECAP, based on the stored propagation time. The waveforms provided at each of the respective electrodes each include a pre-puling component preceding the arrival of the ECAP.

As noted above, the ECAP generally propagates both caudally and rostrally from the point of stimulation. Thus, the direction of ECAP propagation indicated in FIG. 15 may be either caudal or rostral. Some embodiments of the disclosed methods are used to deliver the pre-pulsed second waveforms at caudal sites where collateral terminals of the dorsal column and/or elements in the dorsal horn are believed to innervate the spinal level corresponding to the pain level. According to such embodiments, electrodes E3, E5, E7, E8 are caudal to $E_{Stim}$. However, embodiments of the disclosed methods may be used to deliver pre-pulsing/stimulus rostral to $E_{Stim}$ as well.

It should be noted that other electrode configurations than those illustrated in FIG. 15 may be used, for example, electrode configurations designed to selectively modulate certain horn/column elements with these pre-pulsing waveforms. Moreover, electrodes on one lead may be used to apply the primary stimulus and electrodes on different leads may be used to apply the excitatory/inhibitory pulses, along with pre-pulsing. Further, directional electrodes, paddle leads, and the like may be used.

Figure 16A:
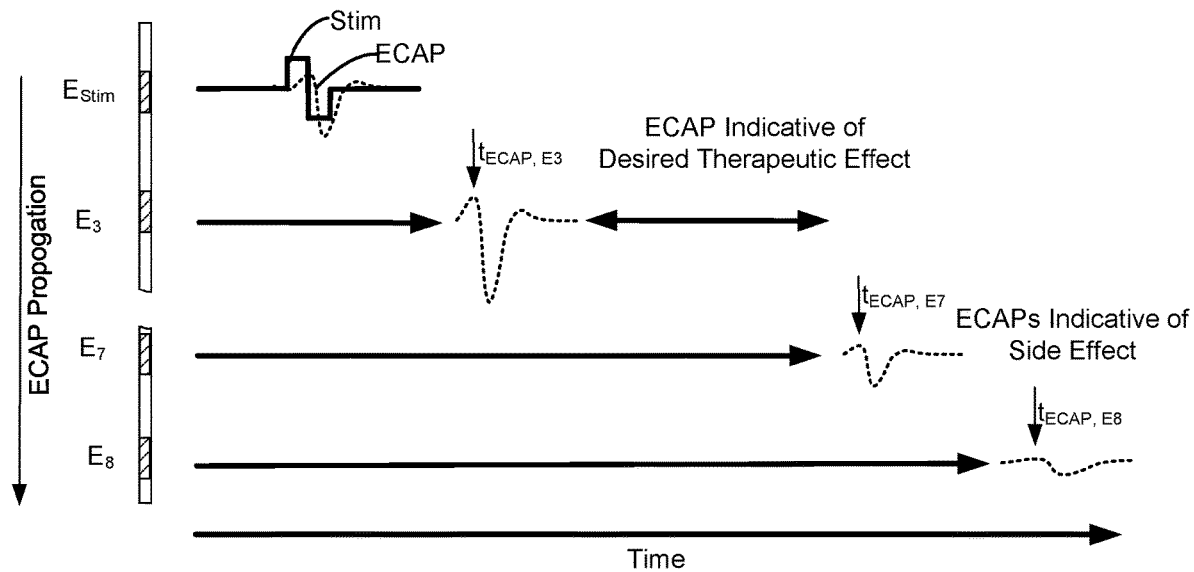
FIGS. 16A and 16B show aspects of an ECAP algorithm.
Figure 16B:
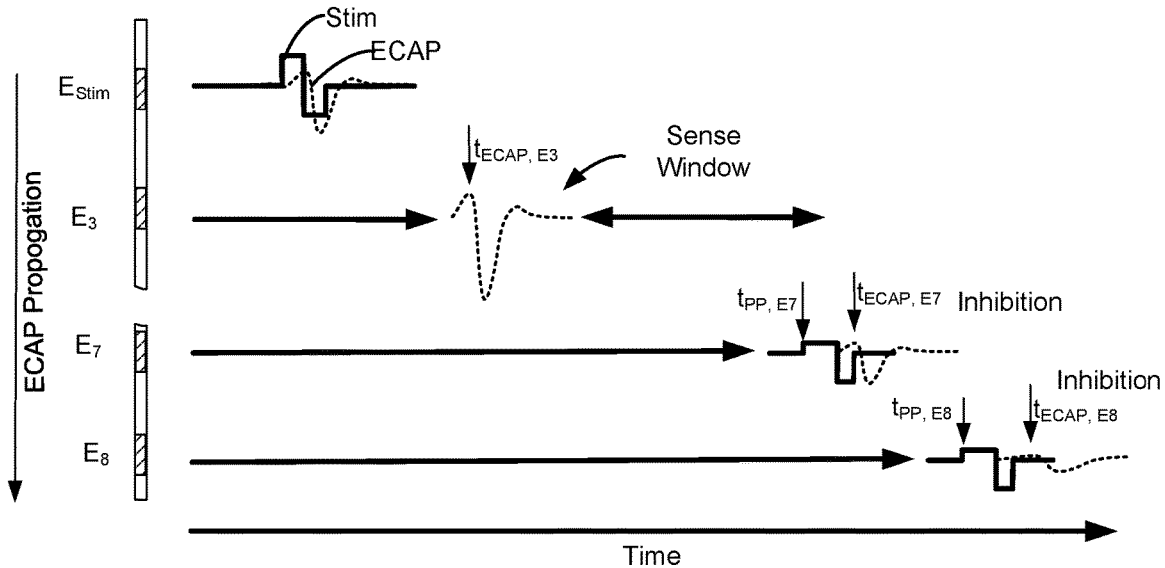

The ECAP algorithm may include additional rules defining how the various stimulation/sensing channels interact to provide excitation or inhibition waveforms triggered using sensed ECAPs. For example, FIGS. 16A and 16B show an embodiment wherein an ECAP sensed at electrode E3 triggers an inhibition waveform on electrodes E7 and E8. Referring to FIG. 16A, assume that during calibration, as described above with reference to FIGS. 14A and 14B, it is determined that when a stimulation waveform Stim is applied at $E_{Stim}$, ECAPs can be sensed at electrodes E3, E7, and E8. Further assume that a strong ECAP at E3 correlates to a desired therapeutic effect and that ECAPs sensed at electrodes E7 and E8 correlate to an unwanted side effect. The running mode of the ECAP algorithm can be programmed such that the application of $E_{Stim}$ triggers a sense window at E3 at a time $t_{ECAP, E3}$ (i.e., the propagation time of the ECAP to E3) as shown in FIG. 16B. If the ECAP is present (and has ECAP metric(s) corresponding to effective therapy), the algorithm is programmed to apply inhibitory pulses at E7 and E8 at times $t_{ECAP, E7}$, and $t_{ECAP, E8}$, respectively, to counteract the neural recruitment responsible for the side effect. Each of the inhibition waveforms illustrated in FIG. 16B include a pre-pulsing component applied at $t_{PP, E7}$ and $t_{PP, E8}$, respectively. Thus, the sensing of an ECAP at E3 triggers inhibitory pulses at E7 and E8. If an ECAP is not sensed at E3, then no inhibitory waveforms are applied at E7 and E8. Moreover, the absence of an ECAP at E3 may cause the algorithm to modify the stimulation pulse parameters of $E_{Stim}$ and/or to apply an excitatory waveform at E3, similar to the E3 excitation pulse illustrated in FIG. 15.

It should be noted that the methods illustrated in FIGS. 15 and 16 both include a calibration mode 1102 and a running mode 1104 as illustrated in FIG. 14. As implemented in the FIGS. 15 and 16 embodiments, the step of determining ECAP Metric(s) 1208 includes determining an ECAP speed or delay, which determines the times for the ECAP to propagate to the sense electrodes, e.g., the times for the ECAP to propagate to E3 ($t_{ECAP, E3}$), E7 ($t_{ECAP, E7}$), and E8 ($t_{ECAP, E8}$). The calibration mode may also determine one or more waveform-sensitive ECAP metric(s) 1212, which the running mode may use to trigger therapy. As mentioned above, the calibration mode 1102 is generally performed with the assistance of a clinician's programmer 90 during the initial fitting procedure.

Each of the embodiments described herein may also include a recalibration process, whereby some or all the calibration steps may be repeated during therapy, for example, in response to the patient's feedback. For example, the patient's external controller 50 may include programming to allow the patient to recalibrate the sensing and recording of ECAPs, the triggering parameters, etc. Moreover, the programming of the IPG 100 (or ETS 170) may include recalibration programming, causing the device to periodically check and adjust the sensing and triggering parameters.

Figure 17A:
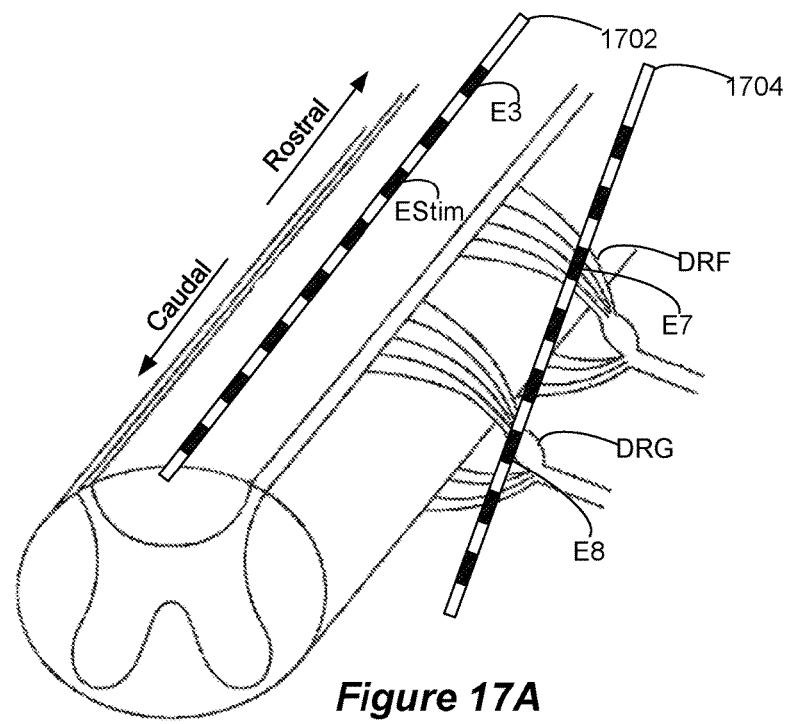
FIGS. 17A and 17B show aspects of an ECAP algorithm.

FIG. 17A illustrates an embodiment where a first lead 1702 is placed along the dorsal column (DC) and a second lead 1704 is placed near the dorsal root ganglia (DRG) and dorsal root fibers (DRF). Inhibitory pre-pulsing at one or more electrodes on the lead 1704 can be used to suppress DRF recruitment, which is responsible for the side effect of rib stimulation. Likewise, inhibitory pre-pulsing at the DRG can suppress recruitment of pain fibers. Excitatory pre-pulsing at electrodes on the lead 1702 may be used to increase neural recruitment, for example, to enhance paresthesia fibers. In each of these examples the effectiveness of the pre-pulses can be monitored and/or modified based on metrics of sensed ECAPs.

Figure 17B:
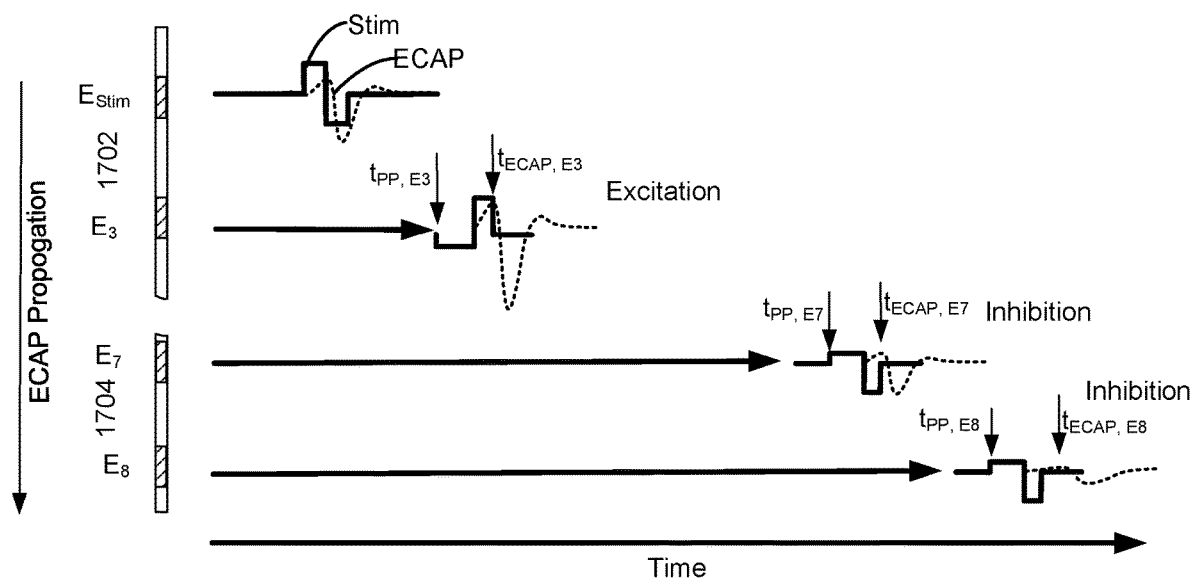

For example, referring to FIG. 17B, assume a stimulation waveform is applied at $E_{Stim}$. During a calibration mode, E3 of electrode lead 1702 and E7 and E8 of electrode lead 1704 can be used to sense ECAPs at those electrodes. The times for ECAPs to reach those electrodes ($t_{ECAP, E3}$, $t_{ECAP, E7}$, and $t_{ECAP, E8}$) can be determined and used to program excitatory and/or inhibitory waveforms triggered based on the stimulation waveform at E3. In the embodiment illustrated in FIG. 17B, an excitatory waveform is delivered on E3 to enhance the ECAP. The excitatory waveform includes a pre-pulse component initiated at $t_{PP, E3}$ preceding the arrival of the ECAP at E3. Inhibitory waveforms are applied to the DRF at E7 and to the DRG at E8. The inhibitory waveforms also include pre-pulsing components initiated at times $t_{PP, E7}$ and $t_{PP, E8}$, respectively, preceding the arrival of the ECAPs to those electrodes.

As with the embodiments described above, the embodiment illustrated in FIGS. 17A and 17B may operate based on metrics derived from the sensed ECAPs (e.g., H_N1, H_N1/H_P2, etc.). The metrics may be used to modify and of the excitatory/inhibitory waveforms in a closed loop fashion during the running mode. For example, the ECAP sensed at E3 may be used to modify the waveform applied at $E_{Stim}$ or the waveform applied at E3 during subsequent pulses. Likewise, the metrics derived from the ECAPs measured at E7 and/or E8 may be used to modify the waveform applied at $E_{Stim}$ and/or the waveforms applied at E7 and E8. For example, metrics derived from the ECAPs sensed at E7 and/or E8 may be used to monitor/predict the dermatomal coverage provided by $E_{Stim}$ and to modify the $E_{Stim}$ waveform accordingly.

The methods and systems described herein provide the sensing of ECAPs and the use of ECAP metrics to monitor and/or adjust stimulation waveforms provided at various electrodes. The waveforms may be excitatory or inhibitory. The stimulation and sensing electrodes may be located on the same or different leads. Moreover, the illustrated examples relate to percutaneous leads. But the same methods and algorithms may be implemented using other types of leads, such as paddle leads (such as lead 15 of FIG. 1A), directional leads, and the like.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A neuromodulation system comprising:
a first device configured to control a plurality of electrodes configured to be implanted in a patient's spinal column, wherein each electrode is configurable to provide electrical stimulation to the patient's spinal cord and/or to sense action potentials in the patient's spinal cord, wherein the first device comprises a microcontroller and a non-transitory computer-readable medium comprising instructions configured to cause the microcontroller to:
cause a first one or more of the electrodes to issue first waveforms to the patient's spinal cord, wherein the first waveforms are configured to evoke action potentials in the patient's spinal cord,
cause a second one or more of the electrodes to record the evoked action potentials evoked in the patient's spinal cord by the first waveforms,
determine at least one feature of the evoked action potentials,
based on the at least one feature, determine whether to issue second waveforms at a third one or more of the electrodes, wherein the third one or more of the electrodes are different than the first one or more of the electrodes,
if it is determined to issue second waveforms:
determine if the second waveforms are enhancing waveforms comprising a pre-pulse component configured to enhance the evoked action potentials or inhibiting waveforms comprising a pre-pulse component configured to inhibit the evoked action potentials, and
trigger the third one or more electrodes to issue the enhancing or inhibiting waveforms to the patient's spinal cord, and
not issue second waveforms if it is determined not to issue second waveforms.

2. The neuromodulation system of claim 1, wherein the third one or more electrodes do not include any of the second one or more electrodes.

3. The neuromodulation system of claim 1, wherein the third one or more electrodes includes at least one of the second electrodes.

4. The neuromodulation system of claim 1, wherein the third one or more electrodes and the second one or more electrodes are the same and wherein the pre-pulse component is triggered before the neural response arrives at the third one or more electrodes.

5. The neuromodulation system of claim 4, wherein the pre-pulse component suppresses the evoked action potential.

6. The neuromodulation system of claim 4, wherein the pre-pulse component enhances the evoked action potential.

7. The neuromodulation system of claim 1, wherein the first device is an implantable pulse generator (IPG).

8. The neuromodulation system of claim 1, wherein the first device is an external programmer for an IPG.

9. The neuromodulation system of claim 1, wherein the first one or more electrodes and the second one or more electrodes are comprised within percutaneous leads.

10. The neuromodulation system of claim 9, wherein the first one or more electrodes and the second one or more electrodes are comprised within the same percutaneous lead.

11. The neuromodulation system of claim 9, wherein the first one or more electrodes and the second one or more electrodes are comprised within different percutaneous leads.

12. The neuromodulation system of claim 1, wherein the first one or more electrodes and the second one or more electrodes are comprised within paddle leads.

13. A method of providing stimulation to a patient's spinal cord, wherein the patient is implanted with one or more electrode leads within their spinal column, each electrode lead comprising a plurality of electrodes, the method comprising:
using a first one or more of the electrodes to issue first waveforms to the patient's spinal column, wherein the first waveforms are configured to evoke action potentials in the patient's spinal cord,
using a second one or more of the electrodes to record the evoked action potentials evoked in the patient's spinal cord by the first waveforms,
determining at least one feature of the evoked action potentials,
using the at least one feature to select second waveforms from a plurality of waveforms comprising enhancing waveforms and inhibiting waveforms, wherein the enhancing waveforms comprise a pre-pulse component configured to enhance the evoked action potentials and the inhibiting waveforms comprise a pre-pulse component configured to inhibit the evoked action potentials,
issuing the selected second waveforms at a third one or more of the electrodes, wherein the third one or more of the electrodes are different than the first one or more of the electrodes.

14. The method of claim 13, wherein the third one or more electrodes do not include any of the second one or more electrodes.

15. The method of claim 13, wherein the one or more secondary stimulus electrodes includes at least one of the sensing electrodes.

16. The method of claim 13, wherein the third electrodes and the second one or more electrodes are the same and wherein the pre-pulse component is triggered before the evoked action potentials arrive at the third one or more electrodes.

17. The method of claim 16, wherein the pre-pulse component suppresses the sensed neural response.

18. The method of claim 16, wherein the pre-pulse component enhances the sensed neural response.

* * * * *